United States Patent [19]

Takahashi et al.

[11] Patent Number: 5,433,105
[45] Date of Patent: Jul. 18, 1995

[54] METHOD AND DEVICE FOR ANALYZING MOISTURE CONTENT IN OIL

[75] Inventors: Kenji Takahashi, Miyagi; Nobuaki Nakarai, Kanagawa, both of Japan

[73] Assignees: Kabushiki Kaisha Komatsu Seisakusho, Tokyo; Komatsu Miyagi Ltd., Miyagi, both of Japan

[21] Appl. No.: 107,131

[22] Filed: Aug. 17, 1993

[30] Foreign Application Priority Data

Aug. 18, 1992 [JP] Japan ................................ 4-240084
Aug. 18, 1992 [JP] Japan ................................ 4-240085
Jul. 7, 1993 [JP] Japan ................................ 5-192775

[51] Int. Cl.⁶ ............................................. G01N 25/00
[52] U.S. Cl. ................................. 73/61.46; 73/61.47
[58] Field of Search ............... 73/61.43, 61.46, 61.47, 73/61.76, 61.77, 61.78, 64.54; 436/40; 374/54, 143

[56] References Cited

U.S. PATENT DOCUMENTS

| | | | |
|---|---|---|---|
| 3,108,829 | 10/1963 | Tolin et al. | 73/61.76 |
| 3,481,182 | 12/1969 | Lineberg | 73/61.47 |
| 3,695,095 | 10/1972 | Lineberg | 73/61.47 |
| 4,251,809 | 2/1981 | Cheney | 73/61.43 |

OTHER PUBLICATIONS

Karl Fisher, "Testing Methods for Water Content of Crude Oil and Petroleum Products", JIS K 2275, 1989.

*Primary Examiner*—Thomas P. Noland
*Assistant Examiner*—Michael J. Brock
*Attorney, Agent, or Firm*—Wenderoth, Lind & Ponack

[57] ABSTRACT

A method for analyzing the moisture content of an oil includes the steps of providing an enclosed chamber sealed in a gas-tight fashion, placing the oil to be analyzed within the enclosed chamber, heating the enclosed chamber for causing the moisture in the oil to evaporate, measuring a parameter that varies depending upon the amount of water vapor generated by the evaporation of the moisture, and deriving a value representative of the moisture content of the oil on the basis of the measured parameter.

15 Claims, 11 Drawing Sheets

METHOD AND DEVICE FOR ANALYZING MOISTURE CONTENT IN OIL

BACKGROUND OF THE INVENTION

1. Field of the Invention

The present invention relates generally to a method and a device for analyzing the moisture content of an oil. More specifically, the invention relates to an analysis of moisture content of an oil, such as an engine oil to be used in an engine mounted on a construction vehicle and so forth, or a working fluid to be used in hydraulic equipment, such as a hydraulic cylinder, or the like.

2. Description of Related Art

As is well known, when moisture, such as water, is comingled with the engine oil of a construction vehicle or the working fluid of hydraulic equipment, the characteristics of the oil can be so degraded by such moisture as to adversely affect the engine or the hydraulic equipment. Therefore, it is important to detect the moisture content of the oil.

Prior art moisture analyzing methods for the oil include a distillation method, Karl Fisher's volume titration method and Karl Fisher's coulomb titration method as discussed in JIS (Japanese Industrial Standard) K2275 "Testing Methods for Water Content of Crude Oil and Petroleum Products". Also, a hot plate method is known in the art as another technique for analyzing the moisture content of the oil. In the latter method, the moisture content is predicted by pouring several drops of oil to be analyzed on an iron plate preliminarily heated to a predetermined temperature (150°, for example), observing the water bubbles and bubbling behavior by eye, and comparing the observed amount of bubbles and bubbling behavior with references derived by the same method with respect to oil having a known moisture content.

The analyzing method recited in the above-mentioned JIS K2275 preferably employs a solvent and Karl Fisher's reagent. Also, this analyzing method requires equipment which is unacceptably large, and a glass instrument, solvent, and reagent. Thus, analysis is cumbersome, the equipment is too large to transport and the glass instrument is easily damaged when it is used at the site of engineering works.

Also, the foregoing hot plate method requires a qualified engineer for making a precise prediction. Furthermore, since it requires oil with a known moisture content, such method is not suitable for use at the site of the engineering works where the construction vehicle is active.

SUMMARY OF THE INVENTION

Therefore, it is an object of the present invention to provide a method and a device for analyzing the moisture content of an oil, which can solve the above problems in the prior art.

Another and more specific object of the present invention is to provide a method and a device for analyzing the moisture content of an oil, which can be implemented even at the site of engineering works where a construction vehicle and construction machines are in operation.

In order to achieve the above-mentioned and other objects, the invention provides a first method for analyzing the moisture content of an oil which comprises the steps of:

defining an enclosed chamber sealed in a gas-tight fashion;

placing the oil to be analyzed within the enclosed chamber;

heating the enclosed chamber for causing the moisture in the oil to evaporate; and measuring a parameter, variable depending upon the amount of water vapor generated by evaporating the oil, for obtaining a value representative of the moisture content of the oil.

Preferably, the enclosed chamber is heated up to a predetermined temperature at which all moisture in the oil is vaporized. The moisture content may be predicted by deriving the value from the expansion of the volume of the chamber produced by the temperature difference between an initial temperature before heating and the predetermined temperature.

On the other hand, the heating step may be initiated before placing the oil to be analyzed within the enclosed chamber, i.e. the oil is placed in the enclosed chamber after the temperature of the enclosed chamber reaches the predetermined temperature.

In the practical implementation, the enclosed chamber has a variable volume, means are provided for maintaining a constant pressure on the gas occupying the chamber, and the parameter is the volume of the enclosed chamber.

Alternatively, the enclosed chamber may have a fixed volume and the parameter is an internal pressure within the enclosed chamber.

A device for analyzing a moisture content of oil comprises:

first means for defining an enclosed chamber sealed in a gas-tight fashion, in which the oil to be analyzed is placed;

second means for heating the enclosed chamber for causing the moisture in the oil to evaporate; and third means for measuring a parameter, variable depending upon the amount of water vapor generated by evaporating the oil, for obtaining a value representative of the moisture content of the oil.

The invention also provided a method for analyzing the moisture content of an oil, which comprises the steps of:

placing the oil to be analyzed within an enclosed chamber which has a variable internal volume;

heating the enclosed chamber to a predetermined temperature;

measuring the amount the volume of the enclosed chamber has changed once the chamber has been heated to the predetermined temperature;

deriving a value representative of a change in the volume of the chamber attributable to the amount of water vapor produced, by subtracting a change in the volume due to the expansion of air within the enclosed chamber from the measured volume change; and determining the moisture content of the oil on the basis of the derived value.

The variable volume enclosed chamber may be initially heated to the predetermined temperature and the oil may be placed within enclosed chamber after the temperature of the enclosed chamber reaches the predetermined temperature, so that the volume change attributable to the expansion of the air is zero. Also, in the preferred method, the enclosed chamber has a variable volume and is sealed in a gas-tight fashion, and the predetermined temperature is selected to be higher than a vapor saturation temperature under a pressure within the enclosed chamber for vaporizing all of the moisture in the oil so that the moisture content of the oil can be determined on the basis of the volume change and the predetermined temperature.

The invention also provides a device for analyzing the moisture content of an oil, which comprises:

an enclosed chamber defined by a main body and a closure lid coupled with the main body in a gas-tight fashion;

a volume variation measuring means cooperating with the enclosed chamber to form a variable volume chamber therewith and for measuring changes in the volume of the variable volume chamber;

a heating means for heating the enclosed chamber in order to convert the moisture contained in the oil into a vapor affecting the volume of the variable volume chamber, whereby the moisture content of the oil can be determined on the basis of the change in volume of the variable volume chamber.

The volume variation measuring means may comprise a pipe having an essentially U-shaped portion communicating with the enclosed chamber and filled with a liquid. Alternatively, the volume variation measuring means may comprise a tube accommodating a piston for defining a cylinder chamber which communicates with the enclosed chamber.

Preferably, the main body is mounted on a base, and the closure lid is pivotably mounted on a ring-shaped support mounted on the base, the support contacting the main body via a seal. The closure lid may have an oil supply port and a ventilation port extending therethrough, and openings for opening and closing the oil supply port and the ventilation port.

The main body may be mounted on a base which has a support block supporting one end of a supporting rod, the supporting rod supporting a ring-shaped support for supporting the closure lid for pivotal movement about a support pin, and a cylinder of the volume variation measuring means is connected to the closure lid.

The invention also provides a method for analyzing the moisture content of an oil, which comprises the steps of:

placing the oil to be analyzed within an enclosed chamber;

heating the enclosed chamber up to a predetermined temperature;

measuring a total pressure within the enclosed chamber at the predetermined temperature; and determining the moisture content of the oil by deriving a partial pressure, attributable to the water vapor produced in the chamber, based on the total pressure.

The invention also provides a method for analyzing the moisture content of an oil, which comprises the steps of:

placing the oil to be analyzed within an enclosed chamber which has a fixed internal volume;

heating the enclosed chamber to a predetermined temperature, the predetermined temperature being selected to be higher than a vapor saturation temperature under a pressure within the enclosed chamber for vaporizing all of the moisture in the oil;

measuring a total pressure within the enclosed chamber at a predetermined temperature; and determining the moisture content of the oil on the basis of the predetermined temperature and the pressure.

The present invention also provides a device for analyzing the moisture content of an oil, the device comprising:

an enclosed chamber with a fixed volume, in which the oil to be analyzed is placed;

heating means for heating the enclosed chamber;

pressure detecting means for detecting an internal pressure within the enclosed chamber; and a temperature detecting means for detecting a temperature in the enclosed chamber, whereby the moisture content of the oil can be determined on the basis of the detected internal pressure and the temperature in the enclosed chamber.

The device may further comprise a temperature sensor disposed in the enclosed chamber and a temperature control means associated with the heating means for controlling the operation of the heating means on the basis of the temperature in the enclosed chamber detected by the temperature sensor.

The enclosed chamber may be defined by a main body and a closure lid detachably and sealingly fitted to the main body, and a container for the oil to be analyzed is placed within the main body. An elongate rod may extend from the container The heating means may be mounted on the outer side surface of at least one of walls defining the enclosed chamber, and has a convering of a heat insulative material.

The invention also provides a method for analyzing the moisture content of an oil, which comprises the steps of:

forming an enclosed chamber by sealingly fitting a closure lid onto an open end of a main body;

preliminarily heating the enclosed chamber until a temperature in the enclosed chamber reaches a predetermined temperature;

releasing the closure lid from the main body and mounting an oil container filled with the oil to be analyzed to the closure lid;

re-fitting the closure lid to the main body by rotating the closure lid so as to introduce the oil in the container into the enclosed chamber, and thereby subjecting the oil in the enclosed chamber to the predetermined temperature for causing the moisture in the oil to evaporate, whereby the moisture in the oil can be determined on the basis of the total pressure in the enclosed chamber and a partial pressure attributable to heated water vapor in the chamber.

The invention also provides a device for analyzing the moisture content of an oil, which comprises:

an enclosed chamber which is preliminarily heated to a predetermined temperature, the enclosed chamber being defined by a vessel main body and a closure lid fitted to the vessel main body;

the closure lid being detachable from the vessel main body by being rotated about the vessel main body;

an oil container detachably mounted to the closure lid; and a pressure measuring means for measuring a pressure within the enclosed chamber so that the moisture content of the oil can be determined on the basis of the total pressure in the enclosed chamber and a partial pressure attributable to heated water vapor in the chamber.

Preferably, hooking jaws are provided at regular circumferential intervals on the outer circumference at the open end of the vessel main body, and the hooking jaws are provided with oblique end faces mating with the closure lid. In this case, the closure lid may be formed with a plurality of grooves at circumferential positions respectively corresponding to the hooking jaws, the grooves having slightly greater widths than those of the hooking jaws.

BRIEF DESCRIPTION OF THE DRAWINGS

The present invention will be understood more fully from the following detailed description and from the accompanying drawings of the preferred embodiments of the invention, which, however, should not be taken to be limitative but are for explanation and understanding only.

In the drawings.

DETAILED DESCRIPTION OF THE PREFERRED EMBODIMENTS

Figure 1:
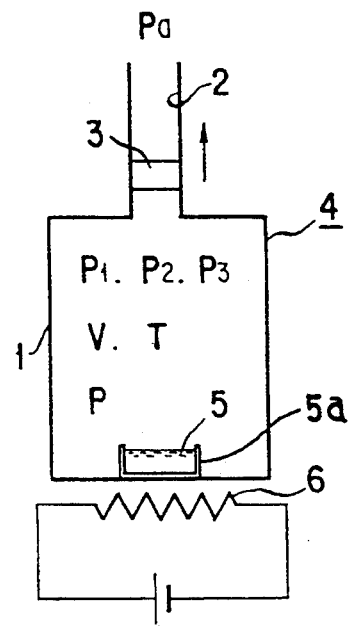
FIG. 1 is a schematic diagram for illustrating a principle behind a first method for analyzing the moisture content of an oil according to the present invention.

Referring now to the drawings, particularly to FIG. 1, the principle behind the first method of the present invention is discussed below for facilitating a better understanding of the invention. A vessel body 1 has a smaller diameter portion 2 extending therefrom. A piston 3 is sealingly and slidingly inserted within the smaller diameter portion 2 for forming an enclosed vessel 4 with a variable volume. Oil 5 contained in a tray 5a is placed within an interior space defined within the vessel body 1.

A heater 6 is provided in opposition to a bottom surface of the vessel body 1 for heating the latter.

In FIG. 1, $P_1$ denotes a partial pressure of a water vapor, $P_2$ denotes a partial pressure of the air, $P_3$ denotes a partial pressure of a vapor of the oil to be analyzed, V denotes a variable internal volume of the enclosed vessel 4, T denotes a temperature [°K.] in the enclosed vessel 4, P denotes a total pressure ($=P_1+P_2+P_3$), and Pa is an atmospheric pressure.

Next, a method for analyzing the moisture content in the oil will be discussed.

(1) By means of the heater 6, the enclosed vessel 4 is heated.

(2) Due to an increase in the temperature T within the enclosed vessel 4, the moisture in the oil to be analyzed is evaporated to increase the internal volume of the enclosed vessel 4. Simultaneously, the air in the enclosed vessel 4 undergoes an equi-pressure expansion to push the piston 3 upwardly to increase of the internal volume.

(3) Then, the total pressure P ($=P_1+P_2+P_3$) of respective partial pressures $P_1$, $P_2$ and $P_3$ is held constant by the action of the piston 3. This can be expressed by $$P=P_a P_0, \ P_0=W_1/A$$

where $W_1$ is a weight of the piston 3, and A is a cross sectional area of the piston 3.

(4) States of the water vapor, air and vapor of the oil to be analyzed at the temperature T become as follows.

(a) State of Water Vapor

The partial pressure $P_1$ of the water vapor becomes a saturated water vapor pressure corresponding to the temperature T in the enclosed vessel 4. Then, equilibrium is established in a state where a part of the moisture is in a form of water vapor and the remainder is held in the liquid in the oil to be analyzed.

(b) State of Vapor of Oil to be Analyzed

The partial pressure $P_3$ of the vapor of the oil to be analyzed becomes a saturated vapor pressure corresponding to the temperature within the enclosed vessel 4. In this condition, equilibrium is established between part of the oil in the vapor phase and the remaining oil in the liquid state. It should be noted that the partial pressure $P_3$ is much smaller than the partial pressure $P_1$ of the water vapor. Therefore, the partial pressure $P_3$ of the oil vapor can be ignored. Also, the amount of the vapor of the oil to be analyzed is small so that most of the oil is held in the liquid phase.

Accordingly, the total pressure P may be considered to be determined only by the partial pressure $P_1$ of the water vapor and the partial pressure $P_2$ of the air. Namely, the following equation (1) can be established:

$$P=(P_1+P_2) \ (P: \text{constant}) \qquad (1)$$

(c) State of the Air

Regarding the air as an ideal gas, Boyle-Charle's law becomes applicable. Here, it can be considered that the water vapor partial pressure $P_1$ is much smaller than the air partial pressure $P_2$ before heating. Therefore, ignoring $P_1$ in the foregoing equation (1), $P=P_2$ can be established.

At the temperature T, $P_2=P-P_1$ is established. Since the pressure before heating is P for the reason set forth above, $$PV_0/T_0=(P-P_1)V/T$$

$$((P-P_1)/P)V=(T/T_0)V_0 \qquad (2)$$

where $T_0$ is a temperature before heating [°K.] ($T_0 = 273 + t_0$);

$V_0$ is an initial volume of the vessel body 4;

V is a volume of the vessel body 4 at the temperature T;

$t_0$ is a temperature [°C.] before heating (corresponding to $T_0$)

(5) By further heating the enclosed vessel 4, all moisture contained in the oil is evaporated. By further heating slightly, the water vapor becomes overheated. The temperature at this state is referred to as $T_1$.

(6) When an equation of state of the gas is applied regarding the water vapor as an ideal gas, the state equation at the temperature $T_1$ can be expressed by:

$$P_1 V_1 = (G/M) R T_1 \tag{3}$$

wherein $P_1$ is a water vapor partial pressure at the temperature $T_1$;

$V_1$ is a volume [m³] of the enclosed vessel at the temperature $T_1$;

G is a weight [kg] of the water vapor;

M is a molecular weight of the water vapor (=18 [kg/kmol]);

R is a gas constant (=848 [kgm/kmol °K.]);

$T_1$ is a temperature [°K.] ($T_1 = 273 + t_1$); and $t_1$ is a temperature [°C.] [corresponding to $T_1$].

(7) The foregoing equations (2) and (3) are solved simultaneously.

Assuming temperature $T = T_1$, $V = V_1$, $$GR/M = (V_1/T_1 - V_0/T_0) P$$

Also, since $V_1 = V_0 + \Delta V$, the foregoing equation can be modified as:

$$G = (M/R)((V_0 + \Delta V)/T_1 - V_0/T_0) \tag{4}$$

From the foregoing equation (4), the amount of the water vapor [kg], i.e. the moisture content contained in the oil to be analyzed, can be derived.

(8) The foregoing G of equation (4) can be expressed with respect to $\Delta V$ as:

$$G = A \cdot \Delta V - B (1/T_0 - 1/T_1) \tag{5}$$

where $A = MP/RT_1$ and $B = MPV_0/R$

Figure 2:
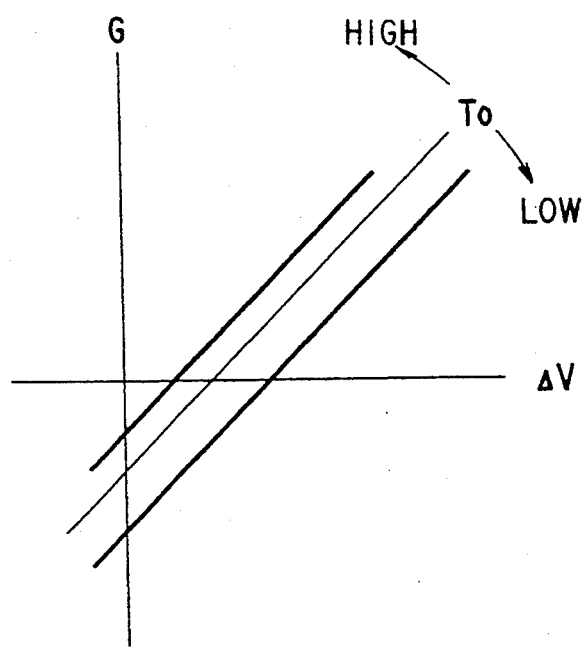
FIG. 2 is a chart showing a relationship between a weight of a water vapor and a volume variation.

The equation (5) can be illustrated as linear graphs as shown in FIG. 2.

As can be appreciated from this graph, when analysis or measurement of the moisture content in the oil is performed while constantly maintaining the temperature at the measurement temperature $T_1$, it can be found that for various temperatures $T_0$ at the analysis starting point, namely whatever atmospheric temperature, the relationships between the weight of the water vapor and the volume variation $\Delta V$ of the enclosed vessel are linear ones which will not plot out parallel to each other.

(9) In order to obtain the moisture content X, assuming the weight of the oil to be measured is W [kg], $$X = (G/W) \times 100 \ [\%]$$

(10) It should be noted that, although this method of analysis does not take into account the water vapor contained in the air, i.e. the influence of humidity, it should be possible to take humidity into account by preliminarily measuring the humidity.

In summary, the analyzing method, according to the present invention, for analyzing the moisture content in the oil measures the variation $\Delta V$ (equi-pressure variation) of the volume of the enclosed vessel 4 at a set temperature $T_1$, derives a volume variation $\Delta V_1$ by the water vapor by subtracting the volume variation $\Delta V_2$ due to the air in the enclosed vessel 4, and predicts the moisture content of the oil to be analyzed on the basis of the volume variation $\Delta V_1$.

With this analyzing method, since no solvent and no reagent are required and no brittle glass instrument is employed, and since the device can be made compact for convenience in use, it can be used even at the site of the engineering works, in which the construction machines are employed for operation.

Modifying the foregoing equation (4), $$\Delta V = ((T_1 - T_0)/T_0) V_0 + (RT_1/MP) G \tag{6}$$

In the foregoing equation (6), the first term represents an influence on $\Delta V$ due to the expansion of the air and the second term represents an influence on $\Delta V$ due to the presence of the moisture.

Here, if the oil to be analyzed is placed in the enclosed vessel 4 after the temperature increases to $T_1$, when the temperature of the oil has is risen to $T_1$ the first term of the equation (6) becomes zero since the initial temperature $T_0$ is $T_1$. Accordingly, in this case, the foregoing equation (6) becomes $$\Delta V = (RT_1/MP) G$$

From this, it should be clearly appreciated that the moisture content is completely proportional to the volume variation. In this way, since there is no volume variation in the first term of the equation (6), an instrument for measuring the internal volume variation of the enclosed vessel 4 can be made smaller.

Practical embodiments for implementing the first aspect of the invention will be discussed with reference to FIGS. 3 to 5.

Figure 3:
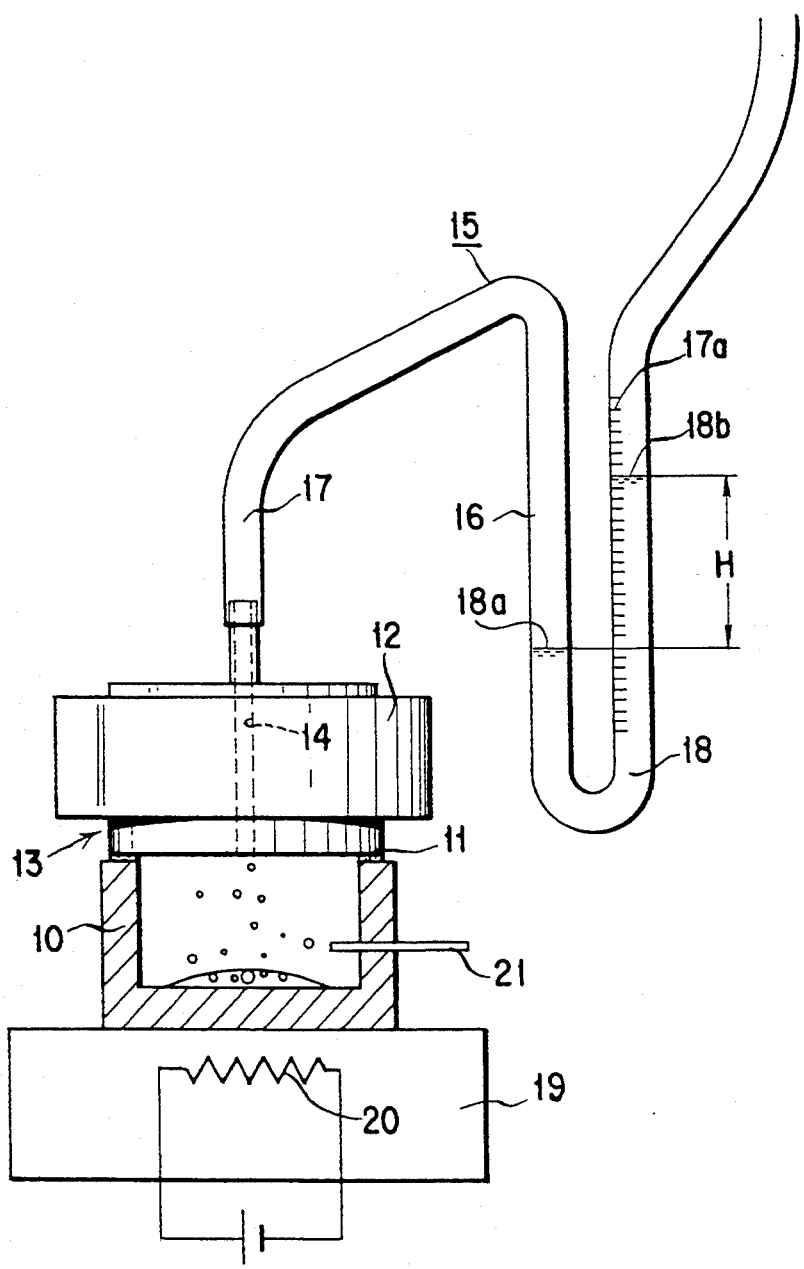
FIG. 3 is a front elevation of the first embodiment of a device for carrying out the first method of analyzing the moisture content of the oil, according to the invention.

FIG. 3 shows the first embodiment of a device for analyzing the moisture content in the oil. As shown in FIG. 3, a closure lid 12 is mounted on an edge of an open end of a vessel body 10 via a sealing member 11, in order to form an enclosed vessel 13. Through the closure lid 12, an opening 14 communicating with the interior space of the vessel body 10 is formed. A volume variation measuring device 15 is connected to the through opening 14. The volume variation measuring device 15 has a pipe-like configuration with a U-shaped portion 16 and a connecting portion 17. The U-shaped portion 16 forms a manometer including a calibration 17a and filling a liquid filling the U-shaped portion. By a difference of the heights of the upper surface 18a at one side and the upper surface 18b at the other side of the U-shaped portion 16 filled with the liquid, and the cross sectional area of the U-shaped portion 16, the volume variation $\Delta V$ in the enclosed chamber 4 can be measured.

With the analyzing device set forth above, the liquid 18 in the U-shaped portion 16 is depressed to cause a difference in height between the upper surface 18a at the one side and the upper surface 18b at the other side so that the variation $\Delta V$ of the internal volume of the enclosed vessel 13 can be detected by reading the calibration 17a. Based on the read difference and a temperature measured by a temperature meter 21, the moisture content in the oil to be analyzed can be predicted.

Figure 4:
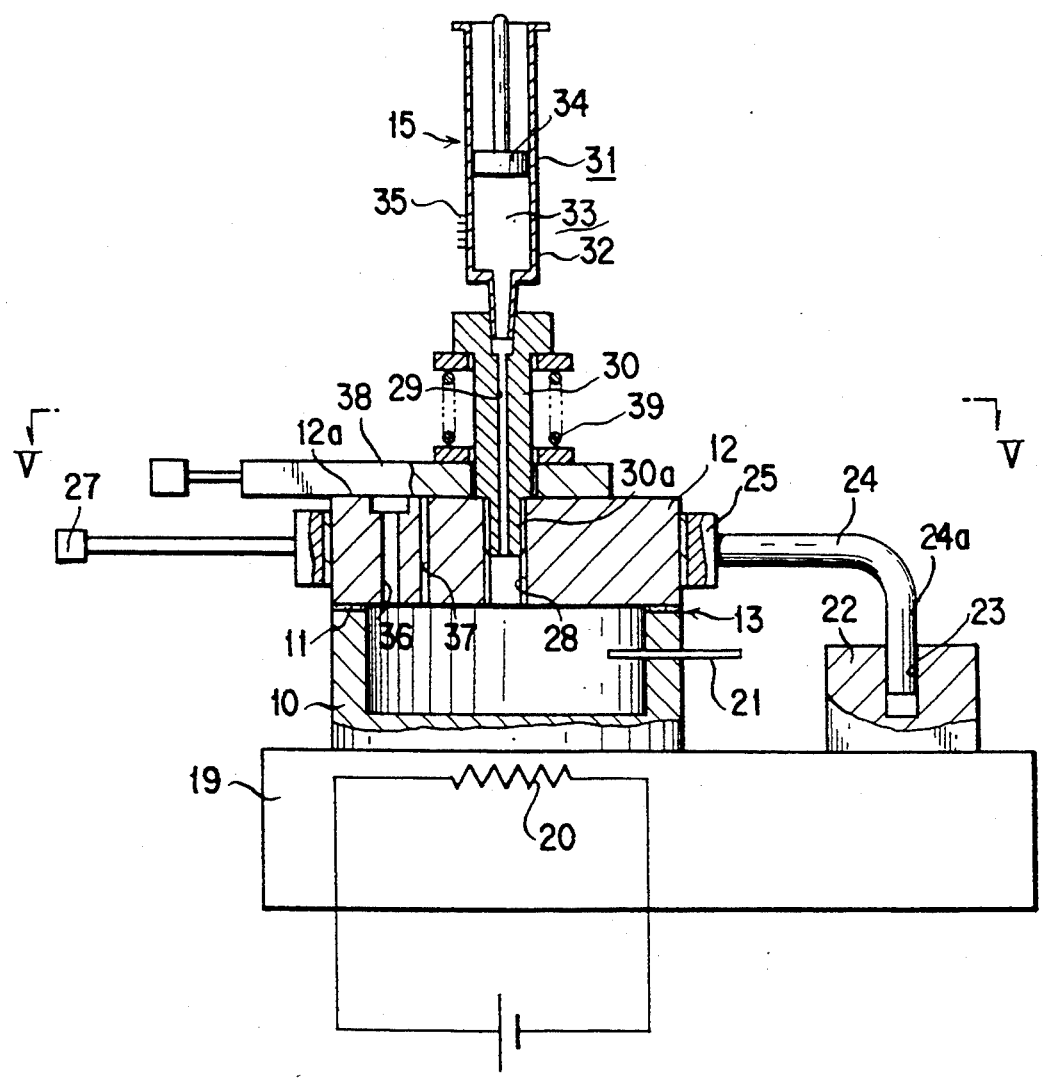
FIG. 4 is a longitudinal sectional view of the second embodiment of the analyzing device for carrying out the first method according to the invention.
Figure 5:
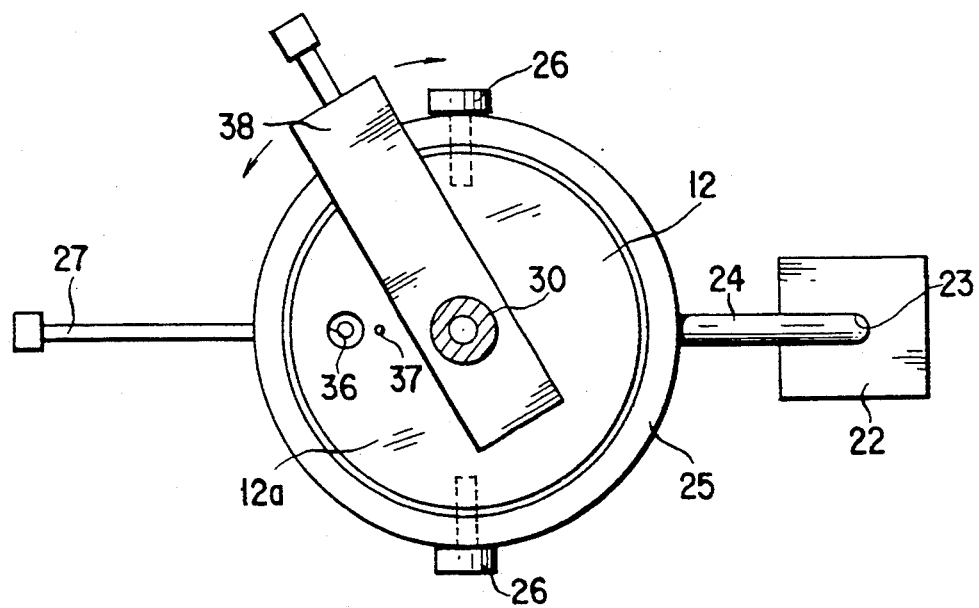
FIG. 5 is a sectional view taken along line V—V of FIG. 4.

FIGS. 4 and 5 show the second embodiment of the moisture content analyzing device according to the first aspect of the invention. A supporting block 22 is mounted on a base 19. A vertically extending opening 23 is formed through the supporting block 22. A vertically bent end 24a of a supporting rod 24 is loosely fitted in the vertically extending opening 23 so as to be pivotal in the horizontal direction and linearly movable in the vertical direction. A support 25 in a form of a ring, is mounted on the supporting rod 24. The closure lid 12 is inserted in and fixed to support 25 by means of supporting pins 26. Also, a handle 27 is provided on the support 25 for pivoting the closure lid 12 in the horizontal direction for opening and closing the upper end of the vessel body 10.

A threaded opening 28 is formed through the closure lid 12. The lower threaded end portion 30a of a shaft 30 mates with the threaded opening 28. A cylinder tube 32 of a cylinder 31 is mounted to the top end of the shaft 30. A cylinder chamber 33 of cylinder 31 and the interior space of the vessel body 10 communicate via an axial hole 29 of the shaft 30 and the threaded opening 28. A calibration 35 is provided on the cylinder tube 32 for allowing the position of a piston 34 disposed in the cylinder tube to be read. With this construction, the volume variation measuring device 15 is formed.

Through the closure lid 12, an oil supply port 36 and a ventilation port 37 are formed to open at the upper surface of the closure lid. A seal plate 38 is pivotably mounted on the upper surface of the closure lid 12 for pivotal movement about the shaft 30. The seal plate 38 is biased toward the upper surface 12a of the closure lid 12 so that the seal plate is fitted to the upper surface of the closure lid in a gas-tight fashion. The seal plate 38 is pivoted to open and close the upper ends of the oil supply port 36 and the ventilation port 37.

With the analyzing device constructed as set forth above, the oil supply port 36 and the ventilation port 37 can be easily opened and closed by pivoting the seal plate 38 to facilitate the supplying of oil into vessel body 10 and the resulting venting of the gas from the interior space of the enclosed vessel. This facilitates measurement of the moisture content in the oil by supplying the oil after the enclosed vessel 13 is heated to the measurement temperature $T_1$.

Although the foregoing first method of the present invention has been described as involving analyzing the moisture content in the oil on the basis of a variation in the volume of the enclosed vessel, a similar analysis can be made on the basis of parameters other than the volume variation, as long as the parameters vary depending upon the amount of the water vapor generated by heating. In the second method of the present invention, the moisture content in the oil is predicted on the basis of a variation in the pressure in the fixed volume of the enclosed vessel. The second method of the present invention will be discussed hereinafter with reference to FIGS. 6 to 12. It should be noted that like parameters will be represented by like reference symbols throughout the drawings.

Figure 6:
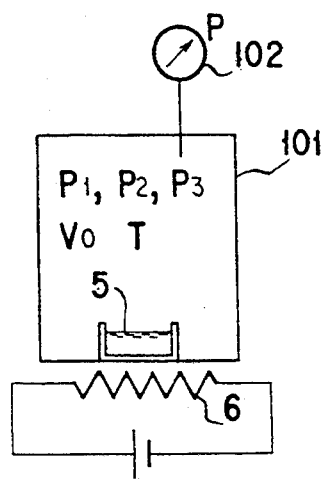
FIG. 6 is a schematic diagram for illustrating a principle behind the second method for analyzing the moisture content of the oil, according to the invention.

Referring to FIG. 6, there is illustrated a principle of the device for analyzing the moisture content of the oil. Differing from the foregoing first embodiment of the invention, the analyzing device for carrying out the second method employs an enclosed vessel 101 having a predetermined fixed volume. Similarly to FIG. 1, $P_1$ denotes a partial pressure of a water vapor, $P_2$ denotes a partial pressure of the air, $P_3$ denotes a partial pressure of a vapor of the oil to be analyzed, $V_0$ denotes an internal volume of the enclosed vessel 101, T denotes a temperature [°K.] in the enclosed vessel 101, P denotes a total pressure ($=P_1+P_2+P_3$), and Pa is an atmospheric pressure.

Next, the method of analyzing the moisture content of the oil will be discussed.

(1) By means of the heater 6, the enclosed vessel 101 is heated.

(2) Due to an increase in the temperature T within the enclosed vessel 101, the moisture in the oil to be analyzed is evaporated to generate the water vapor.

(3) At this time, the respective partial pressures $P_1$, $P_2$ and $P_3$ rise. The behavior of the respective partial pressures while rising in response to an increase in the temperature T will be discussed below.

(a) State of Water Vapor

The partial pressure $P_1$ of the water vapor becomes a saturated water vapor pressure corresponding to the temperature T in the enclosed vessel 101. Then, equilibrium is established in a state where a part of the moisture is in a form of water vapor and the remainder is held in the liquid in the oil to be analyzed.

(b) State of Vapor of Oil to be Analyzed

The partial pressure $P_3$ of the vapor of the oil to be analyzed becomes a saturated vapor pressure corresponding to the temperature within the enclosed vessel 101. In this condition, equilibrium is established between part of oil in the vapor phase and the remaining oil in the liquid state. It should be noted that the partial pressure $P_3$ is much smaller than the partial pressure $P_1$ of the water vapor. Therefore, the partial pressure $P_3$ of the oil vapor can be ignored. Also, the amount of the vapor of the oil to be analyzed is small so that most of the oil is held in the liquid phase.

(c) State of the Air

Regarding the air as an ideal gas, Boyle-Charle's law becomes applicable. Then, the partial pressure of the air can be expressed by:

$$P_0 V_0/T_0 = P_2 V_0/T \quad (V_0: \text{constant})$$

$$\therefore P_2 = (T/T_0) \cdot P_0 \tag{7}$$

where
  $T_0$ is a temperature before heating [°K.] ($T_0 = 273 + t_0$);
  $P_0$ is a pressure upon starting heating (approximately atmospheric pressure); and
  $t_0$ is a temperature [°C.] before heating (correspond to $T_0$)

(4) By further heating the enclosed vessel 101, all moisture contained in the oil is evaporated. By further heating slightly, the water vapor becomes overheated. The temperature at this state is referred to as $T_1$.

(5) A relationship between respective partial pressures $P_1$, $P_2$ and $P_3$ and the total pressure P becomes $$P = P_1 + P_2 + P_3$$

As set forth above, ignoring the partial pressure $P_3$ of the oil vapor, the total pressure P can be expressed as:

$$P = P_1 + P_2 \tag{8}$$

By measuring the total pressure P by means of a pressure sensor 102, and calculating the partial pressure $P_2$ according to the foregoing equation (7), the partial pressure $P_1$ of the water vapor can be derived. It should be noted that, at this time, all of the partial pressures $P_1$, $P_2$ and $P_3$ are absolute pressures instead of gauge pressures.

(6) When an equation of the state of the gas is applied regarding the water vapor as an ideal gas, the state equation at the temperature $T_1$ can be expressed by:

$$P_1V_0 = (G/M) RT_1 \qquad (9)$$

wherein $P_1$ is a water vapor partial pressure at the temperature $T_1$ [kg/m$^2$];

$V_0$ is a volume [m$^3$] of the enclosed vessel;

G is a weight [kg] of the water vapor;

M is a molecular weight of the water vapor (=18 [kg/kmol];

R is a gas constant (=848 [kgm/kmol °K.]);

$T_1$ is a temperature [°K.] ($T_1 = 273 + t_1$); and $t_1$ is a temperature [°C.] [corresponding to $T_1$].

From the foregoing equation (3), the weight [kg] of the water vapor is derived. Namely, G [kg] is the amount of water originally contained in the oil (since all of the moisture is vaporized).

It should be noted that the volume of the oil to be analyzed and the volume of the container to contain the oil can be ignored as negligibly small in comparison with the volume $V_0$ of the enclosed vessel.

Similarly to the foregoing first method of the invention, since no solvent and no reagent are required and no brittle glass instrument is employed, and since the device can be made compact for convenience in use, it can be used even at the site of the engineering works, in which the construction machines are employed for operation.

In order to obtain the moisture content X, assuming the weight of the oil to be measured is W [kg], $$X = (G/W) \times 100 \, [\%]$$

It should be noted that although this method of analysis does not take into account the water vapor contained in the air, i.e. the influence of humidity, it should be possible to take the humidity into account by preliminarily measuring the humidity.

Practical embodiments for carrying out the second method of the invention as set forth above will be discussed hereinafter with reference to FIGS. 7 to 12.

Figure 7:
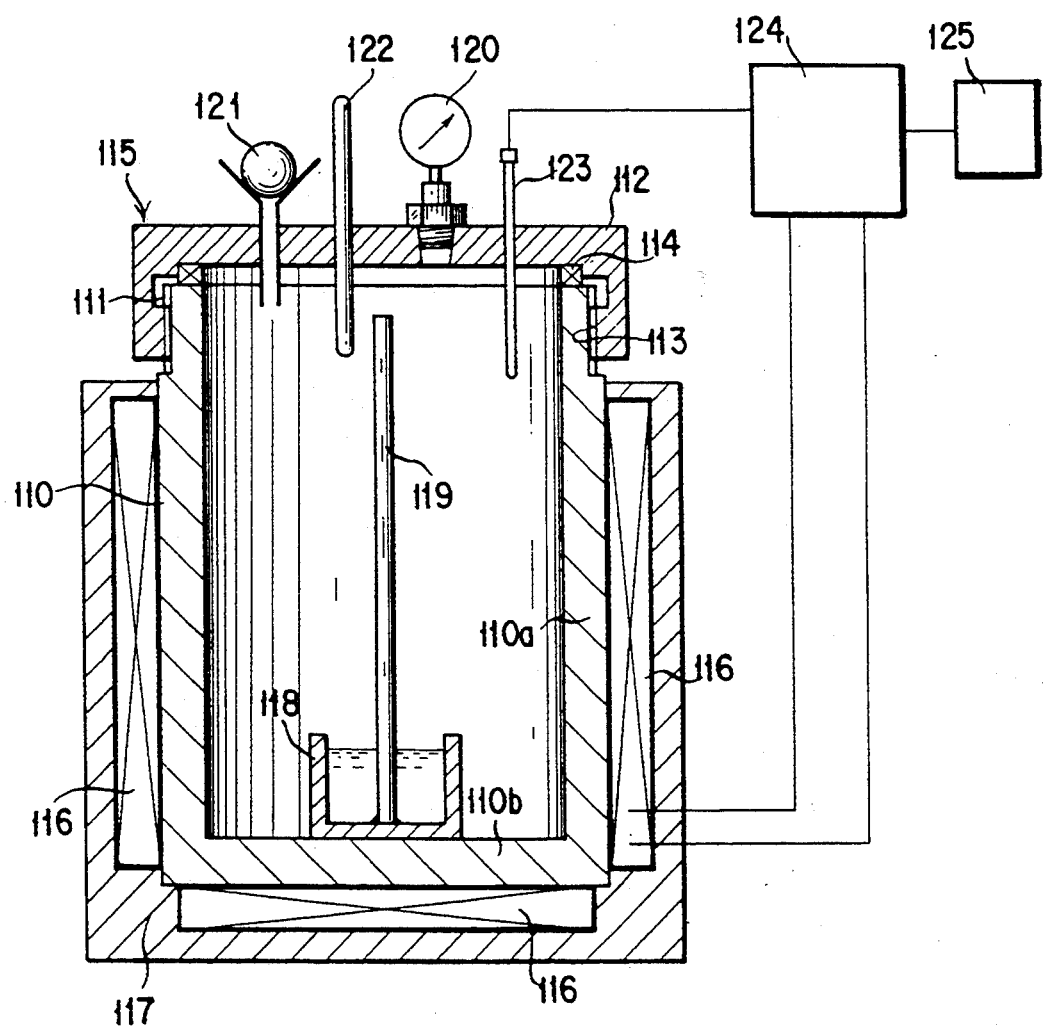
FIG. 7 is a sectional view of the third embodiment of the analyzing device which carries out the second method of analyzing the moisture content of the oil, according to the invention.

FIG. 7 shows the third embodiment which carries out the foregoing second method of the invention. An upwardly opened and essentially cylindrical vessel body 110 is formed with a threaded portion 111. A closure lid 112 has a threaded portion 113 complementary to the threaded portion 111 of the vessel body 110 so that the closure lid 112 may be threadingly fitted to the upper opening end of the vessel body 110. A sealing member 114 is disposed between the top edge of the vessel body 110 and the closure lid 112 for establishing a gas-tight seal to form an enclosed vessel 115. In the circumferential wall 110a and the bottom wall 110b of the vessel body 110, electric heaters 116 are provided for heating the air and oil to be analyzed through thermal transmission, radiation and convection of the air within the enclosed vessel 115. These heaters 116 are covered with a heat insulative member 117 for preventing the heat generated by the heaters 116 from radiating externally.

An oil container 118 filled with the oil to be analyzed is placed on the bottom wall 110b of the vessel body 110. An elongate rod 119 extends vertically from the bottom of the oil container 118 for facilitating the placing of the container is and the removal of the container from the vessel 110.

A pressure meter 120, a safety valve 121 and a temperature meter 122 are mounted on the closure lid 112 for measurement of the internal pressure and the temperature within the internal space of the enclosed vessel 110 and adjustment of the pressure. It should be noted that the safety valve 121 is provided a sufficiently high set pressure so that it can be held inoperative during normal operation.

The closure lid 112 is further provided with a temperature sensor 123 for detecting the temperature in the internal space of the enclosed vessel 115. The temperature sensor 123 feeds a temperature indicative signal to a temperature controller 124. The temperature controller 124 compares the temperature indicative signal with a predetermined set temperature to control the power supply 125 for the heater 116 and adjusts the internal temperature toward the set temperature.

FIGS. 8 to 12 show the fourth embodiment of the moisture content analyzing device for carrying out the second method of the invention. In the shown embodiment, the moisture content analyzing device generally comprises a vessel body 210, a closure lid 220 detachably engaged with the vessel body and rotatable thereabout, an oil cup 230 containing therein the oil to be analyzed, and a pressure detector 240 for measuring the internal pressure within the vessel body 210.

Figure 8:
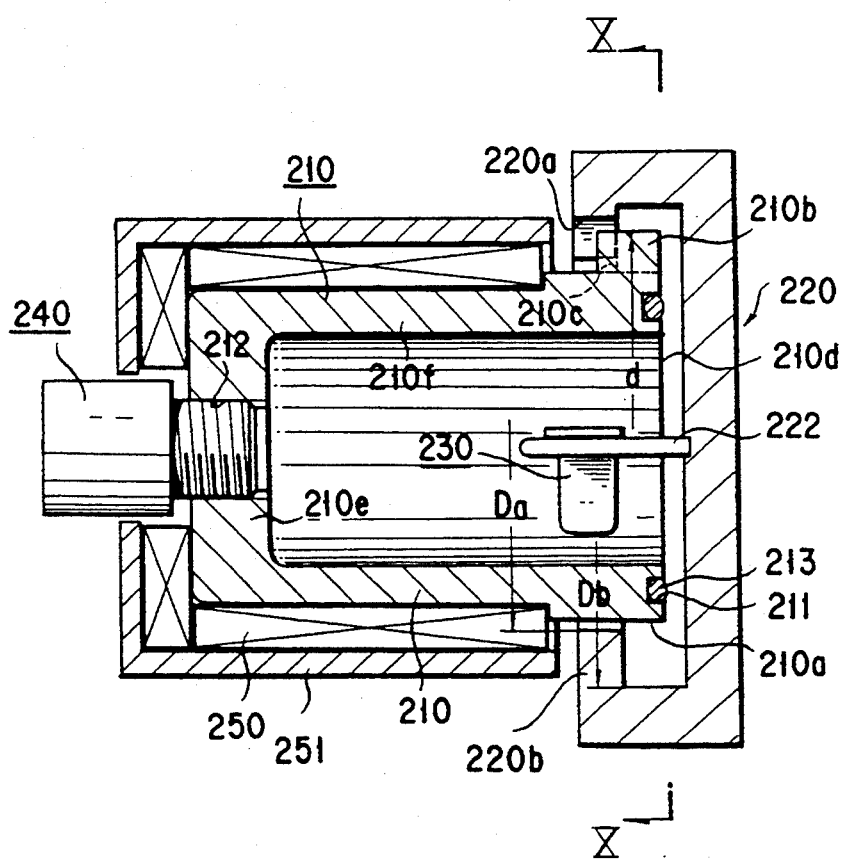
FIG. 8 is a sectional view of a fourth embodiment of the analyzing device, illustrated in a condition before a closure lid is pivoted, for also carrying out the second method, according to the invention.
Figure 9:
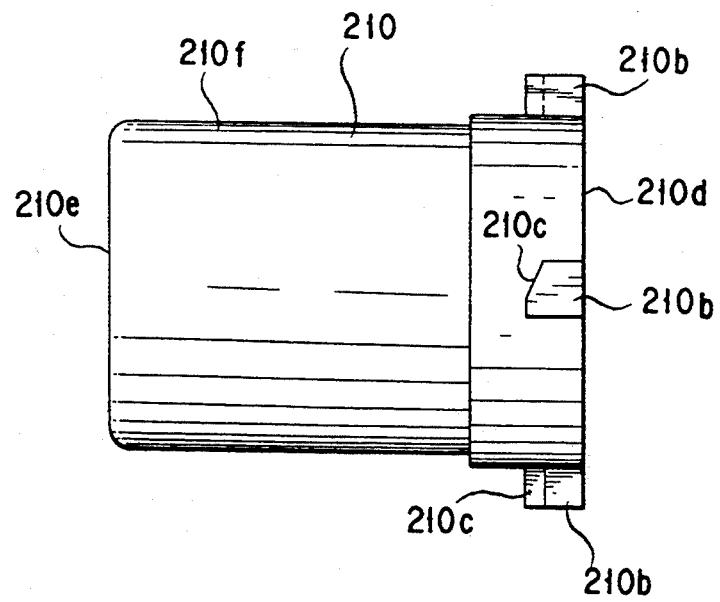
FIG. 9 is a side view of an enclosed vessel of the fourth embodiment of the moisture content analyzing device.
Figure 10:
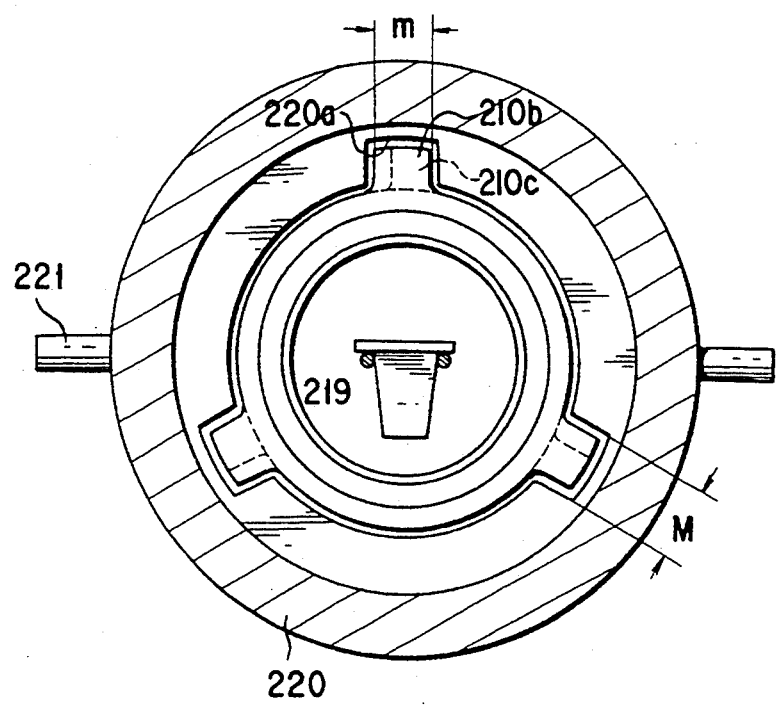
FIG. 10 is a sectional view taken along line X—X of FIG. 8.
Figure 11:
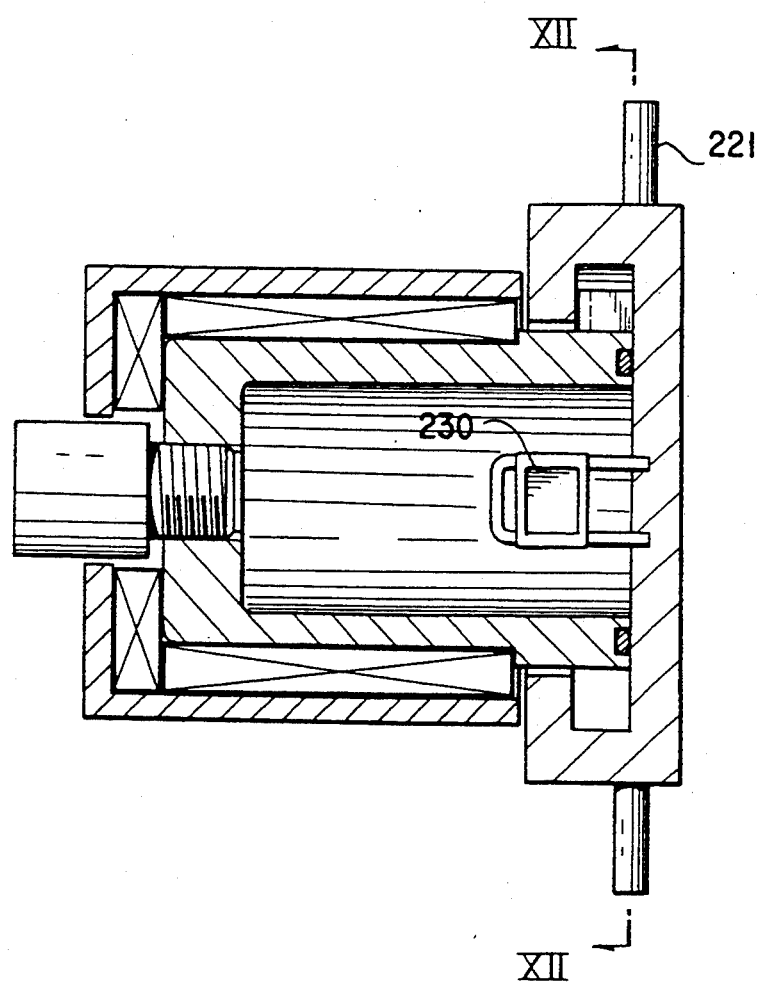
FIG. 11 is a sectional view of the fourth embodiment of the moisture content analyzing device illustrated in a condition after the closure lid has been pivoted.

The vessel body 210 has an essentially cylindrical configuration with an axis oriented substantially horizontally and having one end opened. The vessel body 210 is formed with a plurality of, e.g. two or three, circumferentially arranged hooking jaws 210b extending from the outer periphery 210a of the opened end of the vessel body 210. The hooking jaws 210b are provided with a tapered end 210c defining a surface extending obliquely relative to the opened end 210d of the vessel body 210 and mating with the closure lid 220, as shown in FIG. 8.

A seal receptacle groove 211 is formed on the opened end face of the vessel body 210 for receiving therein a seal member 213. Also, the vessel body 210 is formed with a threaded opening 212 for threadingly accommodating the pressure detector 240.

The closure lid 220 has an essentially dish-shaped configuration with an opened end opposing the opened end of the vessel body 210. An opening diameter (Da) of the lid 220 is smaller than the diameter (Db) of the cylindrical portion thereof. Also, the closure lid 220 has an inwardly extending flange 220b which defines the opening diameter (Da) and is formed with cut-out grooves 220a at circumferential positions corresponding to the hooking jaws 210b of the vessel body 210 and having widths (M) slightly wider than the widths (m) of the hooking jaws 210b, whereby the hooking jaws 210b can be received in the cut-out grooves 220a. On the other hand, the diameter (d) of the hooking jaws 210b of the vessel body 210 is greater than the diameter (Da) of the closure lid 220.

Therefore, the cut-out grooves 220a of the inwardly extending flange 220b of the closure lid 220 are provided in the same number and at the same angular positions as the hooking jaws 210b of the vessel body 210 for facilitating interengagement of the closure lid 220 with the vessel body 210. Also, the closure lid 220 is provided with a pair of hand grips 221 for rotating the closure lid and a pair of support rods 222 for supporting the oil cup 230.

The pressure detector 240 is mounted on the bottom 210c of the vessel body 210 by screwing the detector into the threaded opening 212, whereupon the detector 240 detects the internal pressure within the vessel body 210.

In the circumferential wall and bottom wall of the vessel body 210, an electric heater 250 is disposed. Similarly to the third embodiment, the heater 250 is thermally insulated from the exterior so that external radiation of the heat can be prevented.

Next, the operation of the fourth embodiment of the moisture content analyzing device will be discussed. The oil to be analyzed is preliminarily poured into the oil cup 230. Also, after the opened end of the vessel body 210 is closed by the closure lid 220, the vessel body 210 and the closure lid 220 are heated up to a predetermined temperature. When the predetermined temperature or the temperature near the predetermined temperature is detected by a not shown temperature meter or through measurement of the elapsed time, the closure lid 220 is released from the vessel body 210 while maintaining the temperature condition at the predetermined temperature or at the temperature near the predetermined temperature. Then, the oil cup 230 is placed on the support rods 222 of the closure lid 220. Thereafter, the closure lid 220 while carrying the oil cup 230 is again installed on the vessel body 210. At this time, in order to prevent the oil in the oil cup 230 from spilling, the closure lid 220 is engaged with the vessel body 210 while the hooking jaws 210b are aligned with the cut-out grooves 220a. It may be desirable to provide an eye mark on the outer circumference of the closure lid 220 for indicating the position where the oil cup 230 containing the oil to be analyzed is oriented in the upwardly directed position.

Once the oil cup 230 with the oil to be analyzed is set in the vessel body 210 as illustrated in FIG. 8, the closure lid 220 is rotated about the vessel body 210 toward a predetermined direction (tightening direction) over a predetermined angle with the hand grips 221. At this time, since the surfaces 210c of the hooking jaws 210b are oblique to the opened end face 210d, the vessel body 210 and the closure lid 220 are intimately contact with each other according to rotation of the closure lid along the surfaces 210c. Then, a gas-tight seal is established by the seal member 213 disposed between the vessel body 210 and the closure lid 220.

Figure 12:
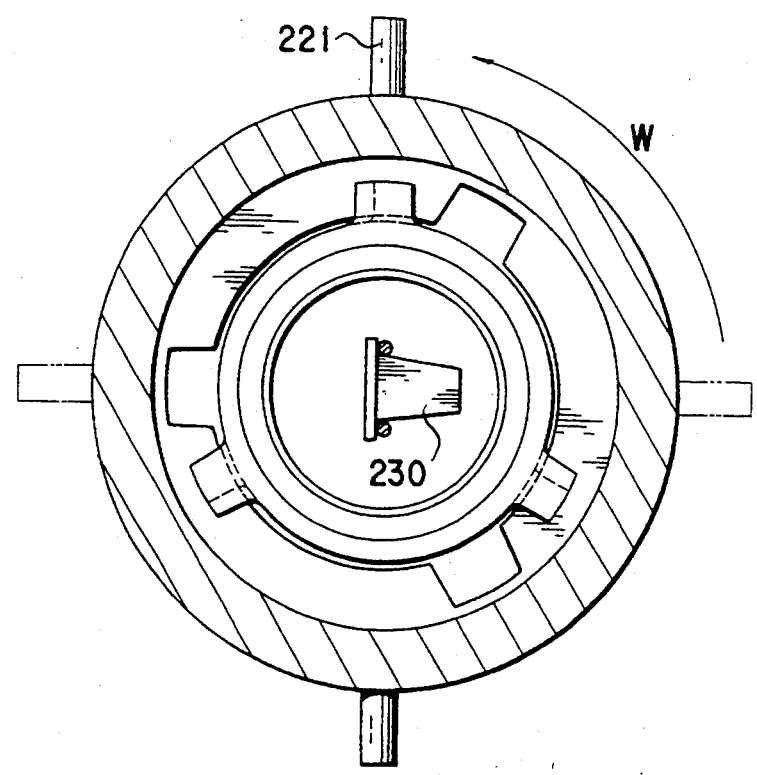
FIG. 12 is a sectional view taken along line XII—XII of FIG. 11.

In the shown embodiment, the closure lid 220 carrying the oil cup 230 filled with the oil to be analyzed is set in the preliminarily heated vessel body 210 and rotated in the direction of W in FIG. 12 over 90°. By this, the vessel body 210 and the closure lid 220 are tightly engaged for establishing the gas-tight seal with the seal member 213. At this time, the oil in the oil cup 230 is thrown into the vessel body 210. It should be noted that the oil cup 230 is provided with a slightly inclined circumferential wall firmly fitted to the supporting rods 222 at the supporting position but allowing its forced separation therefrom. Therefore, even when the closure lid 220 is rotated over 90°, the oil cup 230 will not fall off the support rods 222. (see FIGS. 11 and 12)

As can be appreciated, since the oil to be analyzed is placed in the vessel body simultaneously with the setting of the closure lid, the period required for analyzing the moisture content in the oil is relatively short. Also, since the oil is introduced after fitting the closure lid onto the vessel body 210 in the gas-tight fashion, the water vapor will never escape from the interior space of the vessel body 210, whereby a precise measurement can be effected.

It should be appreciated that, although the oil cup is mounted on the closure lid in the shown embodiment, it may be possible to form the oil cup integrally with the closure lid. In such a case, a plurality of interchangeable integrated lid and cup assemblies are prepared in advance.

Although the invention has been illustrated and described with respect to exemplary embodiments thereof, it should be understood by those skilled in the art that various other changes, omissions and additions may be made therein and thereto without departing from the spirit and scope of the present invention. Therefore, the present invention should not be understood as limited to the specific embodiments set out above but to include all possible embodiments and equivalents thereof within the scope of the appended claims.

What is claimed is:

1. A method for analyzing a moisture content of an oil, said method comprising:
   providing an enclosed chamber having a fixed, invariable internal volume, sealed in a gas-tight fashion, and containing a known amount of gas whose pressure at a predetermined temperature while confined within the chamber is known;
   placing the oil to be analyzed within said enclosed chamber;
   heating the enclosed chamber to said predetermined temperature, said predetermined temperature being sufficient to cause the moisture in the oil to evaporate;
   measuring a parameter that varies depending upon the amount of water vapor generated in the chamber by subjecting the oil to said predetermined temperature; and
   deriving a value representative of the moisture content of the oil on the basis of the measured parameter, including by discounting the influence of the pressure of the gas at said predetermined temperature on said parameter.

2. A method as set forth in claim 1, wherein said enclosed chamber is heated up to a temperature at which all of the moisture in the oil is vaporized.

3. A method for analyzing a moisture content of an oil, said method comprising:
   providing an enclosed chamber sealed in a gas-tight fashion;
   heating the enclosed chamber to a predetermined temperature at which all the moisture in the oil would evaporate before placing the oil to be analyzed within the enclosed chamber;
   placing the oil in the enclosed chamber after the temperature of said enclosed chamber reaches said predetermined temperature; and
   measuring a parameter that varies depending upon the amount of water vapor generated in the chamber by subjecting the oil to said predetermined temperature.

4. Apparatus for use in analyzing the moisture content of an oil, said apparatus comprising:
an enclosed chamber sealed in a gas-tight fashion, in which the oil to be analyzed is to be placed, said enclosed chamber having a fixed, invariable internal volume;
a predetermined amount of gas confined within said chamber, whereby the pressure of said gas at a predetermined temperature while confined within said chamber is known;
a heater operatively associated with said enclosed chamber; and
means for measuring a parameter that varies depending upon the amount of water vapor generated in the chamber by subjecting the oil to said predetermined temperature, whereby the moisture content in the oil can be determined by deriving a value representative of the moisture content on the basis of the measured parameter while discounting the influence of the pressure of the gas at said predetermined temperature on said parameter.

5. A method for analyzing a moisture content of an oil, said method comprising:
providing an enclosed chamber;
heating the enclosed chamber to a predetermined temperature;
placing the oil to be analyzed in the enclosed chamber after the chamber has been heated to said predetermined temperature;
measuring the total pressure within the enclosed chamber at said predetermined temperature; and
quantifying the moisture content of the oil by discounting a partial pressure attributable to the gas within the chamber from the total pressure to derive a partial pressure attributable to water vapor in the enclosed chamber.

6. A method for analyzing a moisture content of an oil, said method comprising:
providing an enclosed chamber having a fixed, invariable internal volume;
heating the enclosed chamber to a predetermined temperature higher than a vapor saturation temperature under a pressure within said enclosed chamber which would vaporize all of the moisture in the oil;
placing the oil to be analyzed in the enclosed chamber after the chamber has been heated to said predetermined temperature to thereby evaporate all of the moisture in the oil;
subsequently measuring the total pressure within the enclosed chamber at said predetermined temperature; and
quantifying the moisture content of the oil on the basis of said predetermined temperature and said pressure.

7. Apparatus for use in analyzing the moisture content of an oil, said apparatus comprising:
an enclosed chamber having a fixed, invariable internal volume, and in which the oil to be analyzed is to be placed;
a predetermined amount of gas confined within said chamber, whereby the pressure of said gas at a predetermined temperature while confined within said chamber is known;
a heater operatively associated with said enclosed chamber so as to heat the chamber;
pressure detecting means for detecting the pressure within said enclosed chamber; and
temperature detecting means for detecting the temperature in said enclosed chamber,
whereby the moisture content of the oil can be determined on the basis of the detected internal pressure, the known pressure of the gas confined in the enclosed chamber, and the temperature in the enclosed chamber.

8. Apparatus as set forth in claim 7, and which further comprises a temperature sensor disposed in said enclosed chamber, and a temperature controller associated with said heater for controlling the operation of said heater on the basis of the temperature in said enclosed chamber detected by said temperature sensor.

9. Apparatus as set forth in claim 7, wherein said main body has at least one wall defining a side of the enclosed chamber, wherein said heater is mounted on the outer side surface of said wall, and wherein said heater includes a heating element covered with a heat insulative material.

10. Apparatus for use in analyzing the moisture content of an oil, said apparatus comprising:
an enclosed chamber having a fixed, invariable internal volume, and in which the oil to be analyzed is to be placed, said enclosed chamber comprising a main body and a closure lid detachably and sealingly fitted to said main body;
a container for accommodating the oil to be analyzed, said container fitting within said main body of the enclosed chamber;
a heater operatively associated with said enclosed chamber so as to heat the enclosed chamber;
pressure detecting means for detecting the pressure within said enclosed chamber; and
temperature detecting means for detecting the temperature in said enclosed chamber,
whereby the moisture content of the oil can be predicted on the basis of the detected internal pressure and the temperature in said enclosed chamber.

11. Apparatus as set forth in claim 10, which further comprises an elongate rod extending from said container.

12. A method for analyzing the moisture content of an oil, said method comprising:
forming an enclosed chamber by providing a vessel main body having an open end, and sealingly fitting a closure lid to the open end of the main body;
preliminarily heating the enclosed chamber until a temperature in the enclosed chamber reaches a predetermined temperature at which moisture in the oil to be analyzed would evaporate;
subsequently releasing the closure lid from the main body and providing an oil container filled with the oil to be analyzed on the closure lid;
re-fitting the closure lid to said main body by rotating the closure lid, such that the oil in the container becomes disposed in said enclosed chamber and is heated at the predetermined temperature to evaporate moisture in the oil; and
determining the moisture content of the oil on the basis of the total pressure in the enclosed chamber and a partial pressure attributed to heated water vapor in the enclosed chamber.

13. Apparatus for use in analyzing the moisture content of an oil, said apparatus comprising:
an enclosed chamber including a vessel main body and a closure lid fitted to said vessel main body, said closure lid having a mount by which the closure lid is securable to and detachable from said vessel main body by rotating said closure lid relative to said vessel main body;

an oil container detachably mounted to said closure lid; and pressure measuring means for measuring the pressure within said enclosed chamber, whereby the moisture content of the oil can be determined on the basis of the total pressure in the enclosed chamber and a partial pressure attributed to heated water vapor in the enclosed chamber.

14. Apparatus as set forth in claim 13, wherein said enclosed chamber includes hooking jaws disposed at regular circumferential intervals on the outer circumference of the open end of said vessel main body, and said hooking jaws having oblique end surfaces mating with the mount of said closure lid.

15. Apparatus as set forth in claim 14, wherein the mount of said closure lid defines a plurality of grooves located at circumferential positions respectively corresponding to said hooking jaws, said grooves having slightly greater widths, taken in the circumferential direction of the lid, than the widths of said hooking jaws as also taken in said direction, respectively.

* * * * *